United States Patent [19]
Chambers

[11] Patent Number: 5,989,247
[45] Date of Patent: Nov. 23, 1999

[54] ELECTRO-SURGICAL INSTRUMENT WITH SPLINE CONNECTION

[75] Inventor: James Ronald Chambers, Littleton, Colo.

[73] Assignee: Smith & Nephew Endoscopy Inc., Andover, Mass.

[21] Appl. No.: 08/649,963

[22] Filed: May 15, 1996

[51] Int. Cl.⁶ .................................................. A61B 17/36
[52] U.S. Cl. ............................................................. 606/41
[58] Field of Search ........................... 606/48–52, 41–46, 606/32–40; 604/20, 21

[56] References Cited

U.S. PATENT DOCUMENTS

| | | |
|---|---|---|
| 1,841,968 | 1/1932 | Lowry . |
| 2,828,747 | 4/1958 | August . |
| 2,888,928 | 6/1959 | Seiger . |
| 3,807,404 | 4/1974 | Weissman et al. . |
| 3,974,833 | 8/1976 | Durden, III . |
| 4,014,343 | 3/1977 | Esty . |
| 4,034,762 | 7/1977 | Cosens et al. . |
| 4,103,688 | 8/1978 | Edwards . |
| 4,593,691 | 6/1986 | Lindstrom et al. . |
| 4,936,842 | 6/1990 | D'Arnelio et al. ........................ 606/42 |
| 5,322,503 | 6/1994 | Desai ........................................ 604/21 |
| 5,324,297 | 6/1994 | Hood et al. ............................... 604/22 |
| 5,540,683 | 7/1996 | Ichikawa et al. .......................... 606/40 |
| 5,609,573 | 3/1997 | Sandock .................................... 606/37 |

FOREIGN PATENT DOCUMENTS

| | | |
|---|---|---|
| 0 484 671 A2 | 5/1992 | European Pat. Off. . |
| 0 698 377 A1 | 2/1996 | European Pat. Off. . |
| 24 60 481 | 6/1976 | Germany . |

OTHER PUBLICATIONS

PCT International Search Report; mailed Oct. 21, 1997; EPO, officer Papone, F.

"Coaxial Bipolar Probe", by David S.C. Pao, M.D., Arch Ophthalmol, vol. 97, Jul. 1979.

*Primary Examiner*—Linda C. M. Dvorak
*Assistant Examiner*—Rosiland Kearney
*Attorney, Agent, or Firm*—Fish & Richardson, P.C.

[57] ABSTRACT

An electro-surgical instrument includes an elongated electrode probe for delivering electrical energy to tissue through an exposed, conductive distal tip and a handpiece that provides the electrical energy to the probe through a coupling to the proximal end of the probe. The coupling, which defines a longitudinal axis, is structured to provide a rigid yet removable connection between the probe and handpiece, and to allow the surgeon to connect the probe to the handpiece at a selected one of several discrete rotational index angles relative to the longitudinal axis.

30 Claims, 1 Drawing Sheet

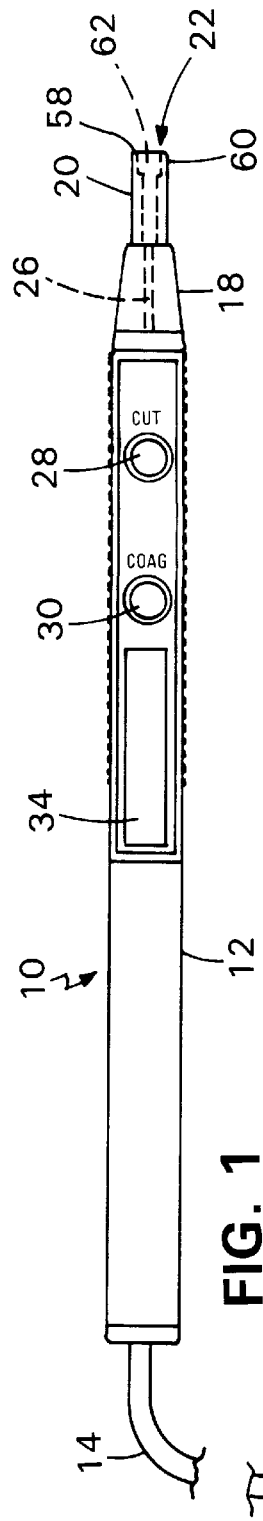
FIG. 1
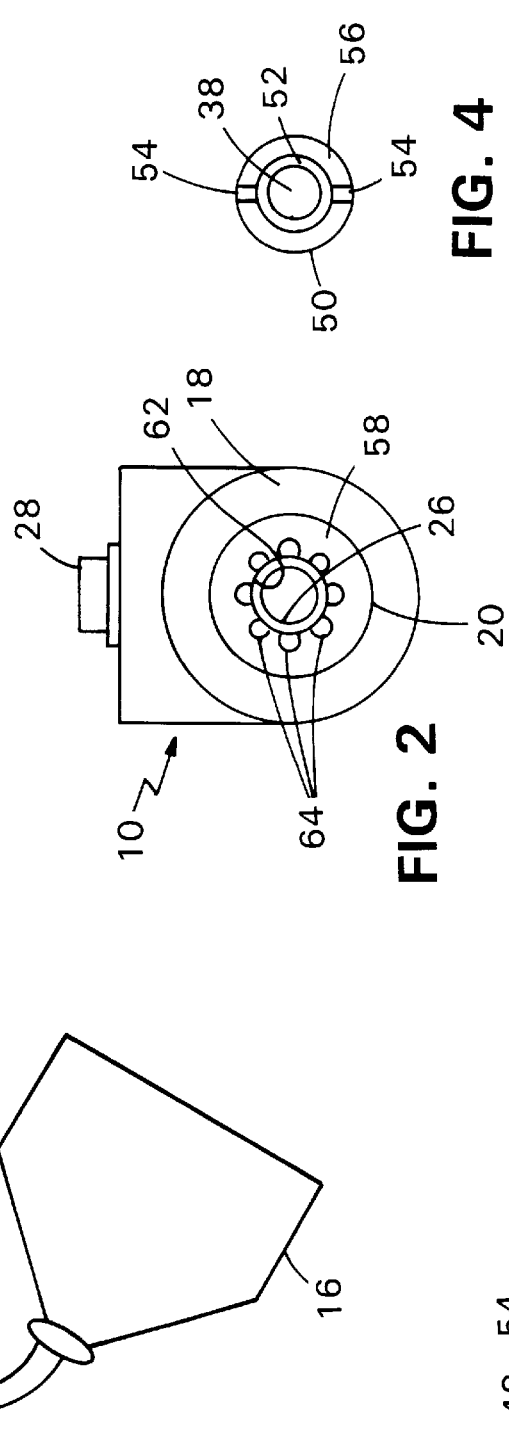
FIG. 2
FIG. 4
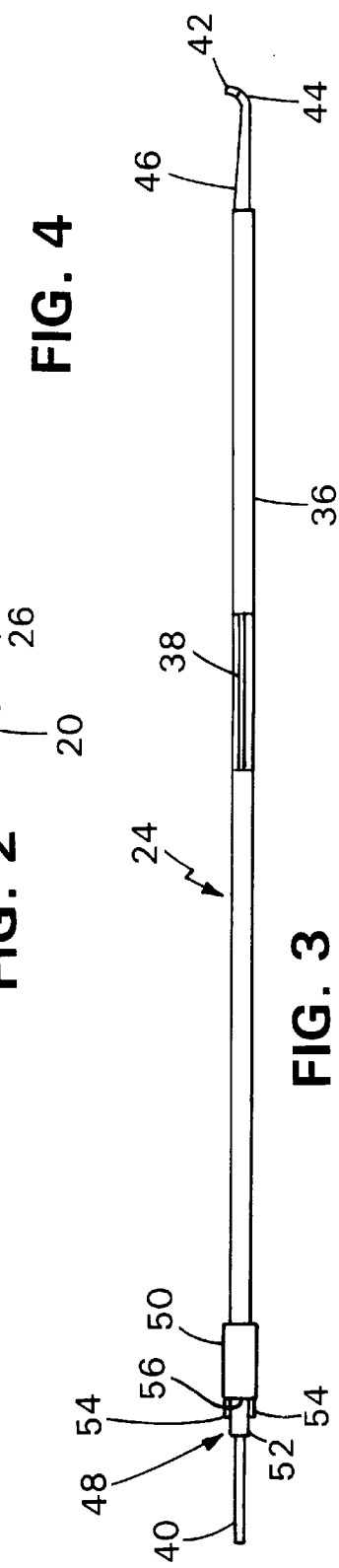
FIG. 3

ELECTRO-SURGICAL INSTRUMENT WITH SPLINE CONNECTION

BACKGROUND OF THE INVENTION

The invention relates to electro-surgical instruments, and, in particular, to an electro-surgical instrument assembly having a coupling between a handpiece and an electrode probe.

Electro-surgical instruments are hand-held devices that have a conducting distal tip through which electrical energy, such as RF energy, is passed to cut or cauterize tissue. The conductive distal tip typically receives the electrical energy via a conductive element, which may include a switch mechanism, built into an insulating body, or handle, of the instrument. The conductive element, in turn, receives the electrical energy from a wire connection to a separate power source. Electro-surgical instruments may be single-piece units or, more commonly, they are configured as two piece assemblies that include a handpiece and an electrode probe that connects to the handpiece.

In the two piece assemblies, the electrode probe typically includes an elongated metallic rod that is insulated to provide electro-surgical action only at a distal end. The conductive distal end may be hooked or otherwise shaped according to specific clinical needs and surgeon preferences. The conductive proximal end of the probe engages with the handpiece. The engagement should provide sufficient structural strength and rigidity to support loads applied during surgery. The engagement also provides electrical contact between switching electronics within the handpiece and the conductive path in the electrode to the distal tip. The two-piece arrangement permits a surgeon to choose from a variety of differently shaped electrode probes for use in different surgical procedures. The handpiece and the electrode probe are usually sterilized and packaged separately, and then assembled together in the surgical theater.

One prior art reference describes a two-piece electro-surgical probe with a keyed retaining chuck for coupling between the probe and the handpiece.

SUMMARY OF THE INVENTION

An electro-surgical instrument, according to the invention, includes a handpiece and an elongated probe with a coupling arrangement that resists rotation of the electrode probe relative to the handpiece and that also permits the surgeon to select one of several rotational index positions of the electrode probe relative to the handpiece. The handpiece has an insulating handpiece body, an input for receiving electrical energy, an electrical terminal at a distal end, and a connection for electrically coupling the input to the terminal. The probe includes an insulating probe body, and an electrode extending therethrough from a proximal end to an exposed conductive distal tip for transmitting electrical energy to tissue. The coupling, formed from the distal end of the handpiece and the proximal end of the probe, is structured for removably and rigidly coupling the probe and handpiece together at a selected one of at least three discrete rotation angles about a longitudinal axis defined by the coupling and for electrically connecting the electrode to the terminal when the handpiece and the probe are coupled together.

According to another aspect of the invention, the coupling is a spline connection, which resists relative rotation of the handpiece and the electrode probe during use. The spline coupling also makes it easy to engage together the handpiece and the electrode probe. Another advantage of the spline coupling is that it includes a plurality of rotational indexing positions of the electrode relative to the switchpen.

According to another feature of the invention, the spline coupling is formed from the insulating bodies of the handpiece and the probe. The electrode and the terminal in the handpiece form a telescope connection, the terminal forming a cylindrical socket, the proximal end of the electrode forming a cylindrical plug that fits into the socket. This feature allows the electrode to function with some prior art handpieces, and the handpiece to function with some prior art electrode probes.

Advantageously, when the invention is used with an electrode that includes a bent distal end, the coupling is structured such that the surgeon can lock the electrode probe in a selected rotational position knowing that the bent end of the electrode is pointed in a desired direction. In one embodiment, the selected rotational positions include a position wherein the bent end is directed 180 degrees from a direction defined by the position of a switch on the handpiece.

BRIEF DESCRIPTION OF THE DRAWING

FIG. 1 is a top plan view of a handpiece according to the invention.

FIG. 2 is an expanded elevation view of the distal end of the handpiece of FIG. 1

FIG. 3 is a partially broken away side elevation view of an electrode probe according to the invention.

FIG. 4 is an expanded elevation view of the proximal end of the probe of FIG. 3.

DETAILED DESCRIPTION OF THE INVENTION

Referring now to FIGS. 1 and 2, a handpiece 10 for an electro-surgical instrument has an elongated, generally cylindrically-shaped insulating body 12. The body can be made of any suitable material that can be sterilized and resterilized, for example, with gamma radiation. Electrical energy is input via a cable 14 connected to a proximal end of the body. The free end of the cable is connected to a three-prong plug 16 for connecting to a power source (not shown). The distal end of handpiece 10 includes a first tapered portion 18 and terminates with a generally cylindrical-shaped nose 20 having a slight taper. The tapered portion 18 and the nose 20 together form a socket 22 for coupling the handpiece 10 to an electrode probe 24 (see FIG. 3). The socket 22 includes an electrical terminal 26 for coupling electric energy to the electrode probe 24, as will be described in greater detail below. The top surface of the body 12 includes two push button switches for coupling the electrical energy from the cable 14 to the terminal 26. One switch 28 couples energy to the probe for cutting tissue, and the other switch 30 couples energy to the probe for denaturing tissue. The sides and bottom of the body 12 around the switches 28, 30 form ridges 32 for easier handling by a surgeon. The top surface of the body 12 in this region of the handpiece 10 also includes a flat panel 34 that can be used to display indicia, such as, for example, a product legend.

Referring now also to FIGS. 3 and 4, an electrode probe for use with the handpiece 10 includes an insulating probe body 36, and a single-piece electrode 38 extending through the insulating body from a proximal end 40 to an exposed conductive distal tip 42. The distal end of electrode 38 may be straight, or, as illustrated in FIG. 3, may be include a bend 44. A clear plastic sleeve 46 leaves only a small portion of the distal tip 42 exposed. Sleeve 46 can be made of any suitable material, for example a fluorocarbon (PTFE) material, and preferably a heat-shrink PTFE material. A central portion of the insulating probe body 36 is made of a plastic material, such as, for example, an olefinic plastic material, and preferably a heat-shrink olefinic plastic. The probe 24 can be sterilized and resterilized for example, with ethylene oxide (ETO) gas.

The proximal end of the probe body 24 forms a male insulating plug 48 for insertion into socket 22 at the distal end of handpiece 10. Insulating plug 48 can be made of a moldable plastic, such as, for example, polystyrene. In the embodiment illustrated in the drawing, plug 48 is molded, at least partially, over the central portion of probe body 36, which has previously been heat shrunk over electrode 38. The proximal end 40 of electrode 38 projects longitudinally beyond the insulating plug 48. Probe 24 is at least about seven inches long from plug 48 to distal tip 42, and is shaped such it can easily fit into a 4.5 mm disposable plastic cannula (not shown), such as, for example, a DYONICS® model 4615, for insertion and removal in the surgical site. In the illustrated embodiment, the taper of the nose 20 of handpiece is approximately 2.148 degrees and is sized to provide a liquid-tight seal with the end of the model 4615 cannula.

Insulating plug 48, like the rest of probe 24, is generally cylindrical-shaped. A distal portion 50 has a larger diameter than most of probe body 24, while a proximal portion 52 has about the same diameter as probe body 24. Proximal portion includes a pair of longitudinally extending ridges, or ribs 54 spaced 180 degrees apart. Ribs 54 extend radially to about the radius of distal portion 50. A shoulder 56 extends radially between the proximal portion 52 and the distal portion 50 of insulating plug 48. Shoulder 56 abuts against a front face 58 of tip 20 when probe 24 is connected to handpiece 10.

Referring now again to FIGS. 1 and 2, socket 22 has an insulating portion 60 having a generally cylindrical inner surface 62 that receives proximal portion 52 of insulating plug 48. Inner surface 62 forms discrete slots, or grooves 64, extending longitudinally from the opening of socket 22 and structured to receive ribs 54. Grooves 64 extend only partially into cylindrical-shaped nose 20, the remainder of which is shaped to closely receive proximal portion 52 of plug 48 when the handpiece 10 and the electrode probe 24 are connected.

In the embodiment illustrated in the drawing, there are eight grooves 66, two of which are aligned in a transverse plane with respect to the longitudinal axis along with switches 28 and 30. However, the invention is not limited to this number of grooves 66. There are preferably at least three, and more preferably at least six evenly spaced grooves 66. The pair of ribs 54 are aligned on the same transverse plane as the bend 44 in electrode 38. By inserting the electrode probe 24 into the handpiece 10 such that the ribs 54 are inserted into the grooves 66 aligned with the switches 28, 30, a surgeon can be assured that the bend 44, and therefore the distal tip 48, is pointed either with the direction defined by the switches or opposite to that direction. By inserting the ribs 54 into a different pair of the grooves 66, the surgeon can select a different operating angle for the tip 48.

It will be appreciated that the above-described spline coupling between the handpiece 10 and the probe 24 allows a surgeon to select the angle at which a curved distal tip 48 of the electrode 38 will face relative to the handpiece 24. Thus, a surgeon can hold the handpiece 10 in a comfortable position while being able to direct the distal tip 42 of the electrode 38 to a desired surgical site.

The described embodiment includes a pair of oppositely directed ribs 54. However, also included in the invention is a plug structured with a single rib or a plug structured with more than two ribs. In fact, there can be as many ribs as there are grooves in the socket. In addition, the ribs may be spaced at less than 180 degrees from each other so long as they are properly spaced to insert into at least two different pairs of grooves.

It will be appreciated that although the described embodiment of the coupling between the probe and the handpiece includes a generally cylindrical-shaped plug and mating socket, other shapes of plugs and mating sockets can also provide a rigid connection that resists rotation and permits the surgeon to select a desired one of several index angles. For example, a hex plug and socket arrangement permits the surgeon to select from six index angles. Other equivalent arrangements will be apparent to those of skill in the art of electro-surgical probes.

It will also be appreciated that although the described embodiment of the coupling between the probe and the handpiece includes an insulating plug formed from the probe and an insulating socket formed from the handpiece, the positions of these structures can be reversed on the probe and handpiece. Similarly, the probe may equivalently include a conductive socket and the handpiece a mating conductive plug for making the electrical connection between the probe and handpiece.

The invention has been described in terms of a particular embodiment. The invention, however, is not limited to the embodiment depicted and described. Rather, the scope of the invention is defined by the appended claims.

What is claimed is:

1. An electro-surgical instrument, comprising:
   a handpiece, including an insulating handpiece body, an input for receiving electrical energy, an electrical terminal at a distal end, and a connection for electrically coupling the input to the terminal;
   an elongated probe including an insulating probe body and an electrode extending therethrough, said electrode comprising a proximal end and an exposed conductive distal tip for transmitting electrical energy to tissue; and
   a coupling defining a longitudinal axis, removably and rigidly coupling the distal end of the handpiece to a proximal end of the probe body at a selected one of at least three discrete rotation angles about the longitudinal axis and enabling electrically connecting the proximal end of the electrode to the terminal when the handpiece and the probe are coupled together, wherein the probe cannot rotate relative to the handpiece when coupled to the handpiece at the selected rotation angle.

2. The electro-surgical instrument of claim 1, wherein the coupling comprises a spline connection formed from the handpiece body and the probe body.

3. The electro-surgical instrument of claim 2, wherein the spline connection includes a generally cylindrical-shaped socket formed from one of the handpiece body and the probe body, the socket comprising a socket surface including a plurality of circumferentially spaced, longitudinally extending grooves, and wherein the spline connection further includes an insulating plug formed from the other of the handpiece body and the probe body, the insulating plug comprising a generally cylindrical outer surface including a longitudinally extending rib structured to engage in a selected one of the grooves when the handpiece and the probe are connected together.

4. The electro-surgical instrument of claim 3, wherein the plurality of grooves comprises at least six evenly spaced grooves.

5. The electro-surgical instrument of claim 3, wherein the outer surface of the insulating plug includes a second longitudinally extending rib for engaging a different one of the grooves.

6. The electro-surgical instrument of claim 5, wherein the plurality of grooves comprises approximately eight evenly spaced grooves.

7. The electro-surgical instrument of claim 3, wherein the insulating plug includes a shoulder at a distal end of the rib.

8. The electro-surgical instrument of claim 3, wherein a proximal end of the rib is longitudinally spaced from a proximal end of the insulating plug.

9. The electro-surgical instrument of claim 3, wherein one of the terminal of the handpiece and the proximal end of the electrode forms a electrical plug and the other of the terminal of the handpiece and the proximal end of the electrode forms an electrical socket structured for receiving the electrical plug when the handpiece and the probe are connected together.

10. The electro-surgical instrument of claim 9, wherein the electrical plug projects longitudinally from the insulating plug.

11. The electro-surgical instrument of claim 10, wherein the insulating plug is formed from the insulating body of the probe and the electrical plug is formed from the proximal end of the electrode.

12. The electro-surgical instrument of claim 1, wherein the connection electrically coupling the input to the terminal comprises a switch having a control on the handpiece.

13. The electro-surgical instrument of claim 12, wherein the switch includes a first switch for applying electrical energy for cutting tissue and a second switch for applying electrical energy for denaturing tissue.

14. The electro-surgical instrument of claim 1, wherein the electrode near the distal tip includes a bend.

15. The electro-surgical instrument of claim 14, wherein the connection electrically coupling the input to the terminal comprises a switch having a control on the handpiece, and wherein one of the discrete rotation angles is aligned such that the probe couples to the handpiece with the bend directed approximately 180 degrees from a direction defined by the switch.

16. The electro-surgical instrument of claim 15, wherein another of the discrete rotation angles is aligned such that the probe couples to the handpiece with the bend directed approximately in the direction defined by the switch.

17. The electro-surgical instrument of claim 1, wherein the probe is shaped such it can easily fit into a 4.5 mm cannula and wherein the distal end of the handpiece is shaped such that it forms a leak-tight connection with an end of the cannula when the probe is coupled to the handpiece.

18. An electro-surgical instrument, comprising:
an elongated handpiece, including an insulating handpiece body, an input for receiving electrical energy, a generally cylindrical-shaped socket defining a longitudinal axis and that comprises an insulating socket surface forming a plurality of circumferentially spaced, longitudinally extending grooves extending from an opening at a distal end of the handpiece and a coaxial, electrically conductive socket surface longitudinally spaced from the grooves, and a switch for electrically coupling the input to the conductive socket surface;
an elongated probe, the probe including an insulating probe body and an electrode extending therethrough, said electrode comprising a proximal end and an exposed conductive distal tip for transmitting electrical energy to tissue, said probe body comprising a generally cylindrical-shaped plug at a proximal end of the probe body, said plug comprising an insulating outer surface forming a pair of circumferentially spaced, longitudinally extending ribs structured to engage in a selected pair of the grooves when the handpiece and the probe are connected together, the proximal end of the electrode projecting longitudinally from the insulating outer surface and being shaped for engaging with the conductive socket surface when the handpiece and the probe are connected together.

19. The electro-surgical instrument of claim 18, wherein the grooves comprise at least six evenly spaced grooves.

20. The electro-surgical instrument of claim 19, wherein the pair of ribs are spaced 180 degrees apart.

21. The electro-surgical instrument of claim 18, wherein the insulating outer surface of the plug forms a shoulder at a distal end of the ribs.

22. The electro-surgical instrument of claim 18, wherein the switch includes a first switch for applying electrical energy for cutting tissue and a second switch for applying electrical energy for denaturing tissue.

23. The electro-surgical instrument of claim 18, wherein the electrode near the distal tip includes a bend.

24. The electro-surgical instrument of claim 23, wherein the ribs are aligned in a plane defined by the bend.

25. The electro-surgical instrument of claim 24, wherein a pair of the grooves extend radially in a plane defined by the switch such that the bend is aligned with the plane defined by the switch when the probe is coupled to the handpiece with the ribs engaged in the pair of the grooves that extend radially in the plane defined by the switch.

26. A handpiece adapted for removably connecting to an electrode probe to thereby form an electro-surgical instrument, the handpiece comprising:
an insulating body;
an input for receiving electrical energy;
a generally cylindrical-shaped socket defining a longitudinal axis and including an insulating interior surface forming a plurality of circumferentially spaced, longitudinally extending grooves extending inwardly from an opening at a distal end of the handpiece and a coaxial, electrically conductive socket surface longitudinally spaced from the grooves; and
a switch for electrically coupling the input to the conductive socket surface.

27. An electro-surgical instrument, comprising:
a handpiece, including an insulating handpiece body, an input for receiving electrical energy, an electrical terminal at a distal end, and an electrical connection electrically coupling the input to the terminal;
an elongated probe including a generally cylindrical-shaped, insulating probe body, and an electrode extending therethrough, said electrode comprising a proximal end and an exposed conductive distal tip for transmitting electrical energy to tissue, wherein the probe is at least seven inches long and shaped to easily fit into a 4.5 mm cannula; and
a coupling defining a longitudinal axis for removably and rigidly coupling the distal end of the handpiece to a proximal end of the probe at a selected one of a plurality of discrete rotation angles about the longitudinal axis such that the Probe cannot rotate relative to the handpiece and for electrically connecting the proximal end of the electrode to the terminal when the handpiece and the probe are coupled together.

28. The electro-surgical instrument of claim 27, wherein the distal end of the handpiece is shaped such that it forms a leak-tight connection with an end of the cannula when the probe is coupled to the handpiece.

29. An elongated electrode probe for coupling to a handpiece to form an electro-surgical instrument, comprising:

an elongated insulating body having a distal end and a proximal end;

an electrode extending through the insulating body, said electrode including a proximal end and a distal tip exposed at the distal end of the body; and a generally cylindrical-shaped plug at the proximal end of the body, including an insulating outer portion comprising a pair of circumferentially spaced, longitudinally extending ribs structured to engage in a selected pair of grooves in a mating socket of the handpiece, the proximal end of the electrode projecting longitudinally from the insulating outer portion and being shaped for engaging with a conductive terminal within the socket when the probe is connected to the handpiece and the ribs are engaged in the selected pair of grooves.

30. A method of coupling an electrode probe to a handpiece to form an electro-surgical instrument, comprising:

providing a handpiece, including an insulating handpiece body, an input for receiving electrical energy, an electrical terminal at a distal end, a connection for electrically coupling the input to the terminal, and a generally cylindrical-shaped socket at a distal end thereof, the socket defining a longitudinal axis;

providing an elongated probe, said probe including an insulating probe body, an electrode extending therethrough, said electrode comprising a proximal end and a distal end, the distal end of the electrode including a bend and an exposed conductive distal tip for transmitting electrical energy to tissue, said body comprising a plug at a proximal end, the plug being structured for inserting into the socket at a selected one of at least three discrete index angles relative to the longitudinal axis; and inserting the plug into the socket such that the probe is rigidly coupled to the handpiece at one of the discrete index angles, such that the probe cannot rotate relative to the handpiece and such that the electrode is electrically connected to the terminal.

* * * * *

UNITED STATES PATENT AND TRADEMARK OFFICE
CERTIFICATE OF CORRECTION

PATENT NO. : 5,989,247
DATED : NOVEMBER 23, 1999
INVENTOR(S) : JAMES RONALD CHAMBERS

It is certified that error appears in the above-identified patent and that said Letters Patent is hereby corrected as shown below:

On the title page:
    under the heading Assignee: please delete "Smith & Nephew Endoscopy, Inc., Andover, Mass." and replace with --Smith & Nephew, Inc., Memphis, Tenn.--

Signed and Sealed this

Twenty-second Day of May, 2001

Attest:

NICHOLAS P. GODICI

*Attesting Officer*    *Acting Director of the United States Patent and Trademark Office*